United States Patent
Chaghajerdi et al.

(10) Patent No.: US 10,033,308 B2
(45) Date of Patent: Jul. 24, 2018

(54) SYSTEMS AND METHODS FOR MOTOR TORQUE COMPENSATION

(71) Applicant: Intuitive Surgical Operations, Inc., Sunnyvale, CA (US)

(72) Inventors: Amir Chaghajerdi, Sunnyvale, CA (US); Pushkar Hingwe, Los Gatos, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 558 days.

(21) Appl. No.: 14/660,282

(22) Filed: Mar. 17, 2015

(65) Prior Publication Data

US 2016/0270779 A1    Sep. 22, 2016

(51) Int. Cl.
| | |
|---|---|
| *H02P 6/10* | (2006.01) |
| *A61B 34/35* | (2016.01) |
| *A61B 34/00* | (2016.01) |
| *H02P 29/50* | (2016.01) |
| *A61B 17/072* | (2006.01) |
| *A61B 17/00* | (2006.01) |
| *A61B 90/00* | (2016.01) |

(52) U.S. Cl.
CPC ................ *H02P 6/10* (2013.01); *A61B 34/35* (2016.02); *A61B 34/70* (2016.02); *H02P 29/50* (2016.02); *A61B 17/07207* (2013.01); *A61B 2017/00398* (2013.01); *A61B 2090/031* (2016.02); *A61B 2090/066* (2016.02)

(58) Field of Classification Search
CPC . H02P 6/10; H02P 29/50; A61B 34/35; A61B 17/10; A61B 17/068; A61B 17/072

USPC ...................... 227/175.1, 176.1, 19; 606/142
See application file for complete search history.

(56) References Cited

U.S. PATENT DOCUMENTS

| | | | |
|---|---|---|---|
| 9,522,003 B2 | 12/2016 | Weir et al. | |
| 2007/0151389 A1 | 7/2007 | Prisco et al. | |
| 2008/0046122 A1* | 2/2008 | Manzo | A61B 1/00149 |
| | | | 700/245 |
| 2008/0084173 A1* | 4/2008 | Grabinger | G05B 19/19 |
| | | | 318/432 |
| 2009/0088774 A1* | 4/2009 | Swarup | A61B 34/37 |
| | | | 606/130 |

(Continued)

FOREIGN PATENT DOCUMENTS

| | | |
|---|---|---|
| JP | 2002219136 A | 8/2002 |
| JP | 2007202344 A | 8/2007 |

(Continued)

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

(Continued)

*Primary Examiner* — Nathaniel Chukwurah

(57) ABSTRACT

A method includes receiving a torque limit for a motor, monitoring a torque output of the motor, determining an amplitude and a phase of a torque ripple of the torque output, and determining a compensated torque limit for the motor, the compensated torque limit including a first component at the torque limit and a second component at an adjusted torque limit.

15 Claims, 8 Drawing Sheets

(56) References Cited

U.S. PATENT DOCUMENTS

| | | | |
|---|---|---|---|
| 2012/0205419 A1* | 8/2012 | Weir | ................ A61B 17/07207 227/2 |
| 2014/0200596 A1* | 7/2014 | Weir | ................ A61B 17/07207 606/142 |
| 2014/0200612 A1 | 7/2014 | Weir et al. | |
| 2014/0200851 A1 | 7/2014 | Weir et al. | |
| 2014/0200956 A1 | 7/2014 | Weir et al. | |
| 2017/0179857 A1 | 6/2017 | Liao et al. | |

FOREIGN PATENT DOCUMENTS

| | | | |
|---|---|---|---|
| JP | 2008306801 A | | 12/2008 |
| KR | 20140026875 A | | 3/2014 |
| WO | WO-2014110561 A1 | | 7/2014 |
| WO | WO-2014110564 A1 | | 7/2014 |
| WO | WO-2016187008 A1 | | 1/2017 |

OTHER PUBLICATIONS

International Search Report and Written Opinion for Application No. PCT/US2016/022486, dated Jul. 11, 2016, 11 pages.

\* cited by examiner

SYSTEMS AND METHODS FOR MOTOR TORQUE COMPENSATION

FIELD

The present disclosure is directed to systems and methods for motor torque compensation, and more particularly to systems and methods for efficiently compensating for torque output variations for specific motors.

BACKGROUND

Electric motors are commonly used in a variety of applications. Such motors are electric machines that generate torque (or force, in the case of a linear motor) when supplied with an electric current. Electric motors may be used in a variety of applications. For example, teleoperative surgery involves the use of manipulator arms that move a medical instrument in a variety of spaces. The medical instrument at the end of a manipulator arm may be driven by an electric motor. For example, a stapler instrument may be attached to the distal end of a manipulator arm. A motor positioned proximal to the manipulator arm may be connected to the stapler through a system of drive-shafts and universal joints. Connecting the motor to such a system puts a load on the motor that causes the torque output of the motor to exhibit a torque ripple. The torque ripple creates an oscillation component in the torque output.

Sensor systems are used to safely and effectively operate the motor to provide the forces needed to accommodate, for example, a maximum tissue thickness for a stapler. For example, sensor systems may be used to ensure that the torque output does not exceed a predefined torque limit. When torque ripple occurs, the predefined maximum motor torque limit may be uniformly changed to accommodate the oscillation component of the torque output. However uniformly changing the maximum motor torque limit changes the tissue thickness that the stapler can routinely accommodate. Systems and methods are needed to allow for safe and effective operation of the motor while accommodating the forces needed by the stapler to accommodate maximum tissue thickness.

SUMMARY

The embodiments of the invention are best summarized by the claims that follow the description.

According to one example, a method includes receiving a torque limit for a motor, monitoring a torque output of the motor, determining an amplitude and a phase of a torque ripple of the torque output, and determining a compensated torque limit for the motor, the compensated torque limit including a first component at the torque limit and a second component at an adjusted torque limit.

According to one example, a method includes monitoring a torque output of a motor, receiving an upper torque limit for the motor, determining an oscillation component of the torque output, the oscillation component being associated with a torque ripple, adjusting the upper torque limit based on the determined oscillation component to create a locally compensated upper torque limit, and comparing the torque output to the locally compensated upper torque limit.

According to one example, a medical instrument system includes a motor and a control system comprising a processor and a memory, the memory comprising machine readable instructions that when executed by the processor, cause the control system to: monitor a torque output of a motor, determine an oscillation component of the torque output, the oscillation component being associated with a torque ripple, receive an upper torque limit, adjust the upper torque limit based on the oscillation component to create a localized compensated upper torque limit, output to a user interface, an indication of operation failure in response to a determination that the torque output exceeds the localized compensated upper torque limit.

According to one example, a medical instrument system includes a motor and a control system comprising a processor and a memory, the memory comprising machine readable instructions that when executed by the processor, cause the control system to: receive a motor torque limit for a motor, monitor a torque output of the motor, determine an amplitude and a phase of a torque ripple of the torque output, and determine a locally compensated torque limit for the motor based on the torque ripple.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DETAILED DESCRIPTION

Figure 1A:
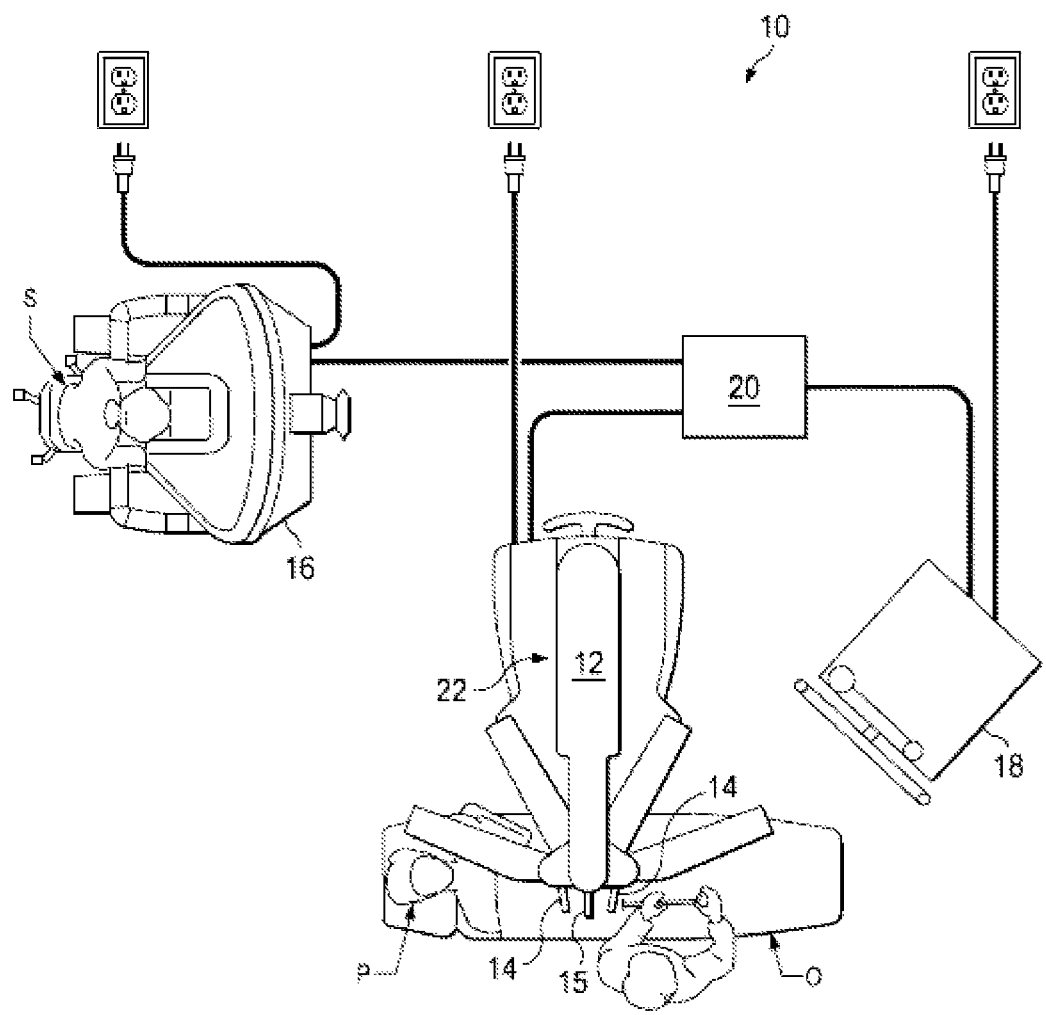
FIG. 1A is a schematic view of a teleoperational medical system, in accordance with an embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

As described above, loads placed on a motor may cause the torque output of the motor to exhibit a torque ripple in order to compensate for any oscillations. Traditionally, the predefined maximum motor torque limit is changed to accommodate the oscillation component of the torque output. However, changing the maximum motor torque limit changes the effectiveness of the instrument powered by the motor. For example, lowering the maximum motor torque limit reduces tissue thickness that the stapler can accommodate. According to principles described herein, a dynamic, adaptive torque limit is used. Such a torque limit compensates for the torque ripple in real time. Specifically, a torque limit for a particular operation of the motor is received. During operation of the motor, characteristics of the torque ripple are determined in real-time. As will be described in more detail, the torque ripple may vary in real time based on a variety of factors. Using obtained information related to the torque ripple, the received torque limit is adjusted in real time to create a dynamic torque limit. The dynamic torque limit may also be referred to as a compensated torque limit as the torque limit is adjusted dynamically to compensate for oscillations in the torque output. The dynamic torque limit is thus used in place of the originally received torque limit. If the torque output of the motor exceeds the dynamic torque limit, then the control system can respond. For example, the control system may alert an operator of the instrument being driven by the motor that a failure of the operation may have occurred.

Use of such a dynamic torque limit may be advantageous in a variety of situations. In one example, a stapler instrument for a teleoperational surgical system may be driven by a motor. For certain operations of the stapler mechanism, there may be a limit on the torque output of the motor. If such a limit is reached, it may indicate that the operation was not performed correctly or in order to control the tissue thickness the output torque should not exceed a calibrated limit. Thus, the teleoperational surgical system may be configured to alert a user to the possible operation failure. But, due to the torque ripple that is experienced by the motor driving the stapler instrument, such an alert may be unnecessarily triggered. Using the dynamic limit described herein prevents such alerts. The principles described herein related to a dynamic torque limit are described in the context of a stapler instrument for a teleoperational surgical system. It is understood, however, that such dynamic torque limits may be used in other situations that involve monitoring the torque output of a motor that drives a mechanical system.

Referring to FIG. 1A of the drawings, a teleoperational medical system for use in, for example, medical procedures including diagnostic, therapeutic, or surgical procedures, is generally indicated by the reference numeral 10. As will be described, the teleoperational medical systems of this disclosure are under the teleoperational control of a surgeon. In alternative embodiments, a teleoperational medical system may be under the partial control of a computer programmed to perform the procedure or sub-procedure. In still other alternative embodiments, a fully automated medical system, under the full control of a computer programmed to perform the procedure or sub-procedure, may be used to perform procedures or sub-procedures. As shown in FIG. 1A, the teleoperational medical system 10 generally includes a teleoperational assembly 12 mounted to or near an operating table O on which a patient P is positioned. The teleoperational assembly 12 may be referred to as a patient side cart. A medical instrument system 14 is operably coupled to the teleoperational assembly 12. An operator input system 16 allows a surgeon or other type of clinician S to view images of or representing the surgical site and to control the operation of the medical instrument system 14.

The operator input system 16 may be located at a surgeon's console, which is usually located in the same room as operating table O. It should be understood, however, that the surgeon S can be located in a different room or a completely different building from the patient P. Operator input system 16 generally includes one or more control device(s) for controlling the medical instrument system 14. The control device(s) may include one or more of any number of a variety of input devices, such as hand grips, joysticks, trackballs, data gloves, trigger-guns, hand-operated controllers, voice recognition devices, touch screens, body motion or presence sensors, and the like. In some embodiments, the control device(s) will be provided with the same degrees of freedom as the medical instruments of the teleoperational assembly to provide the surgeon with telepresence, the perception that the control device(s) are integral with the instruments so that the surgeon has a strong sense of directly controlling instruments as if present at the surgical site. In other embodiments, the control device(s) may have more or fewer degrees of freedom than the associated medical instruments and still provide the surgeon with telepresence. In some embodiments, the control device(s) are manual input devices which move with six degrees of freedom, and which may also include an actuatable handle for actuating instruments (for example, for closing grasping jaws, applying an electrical potential to an electrode, delivering a medicinal treatment, and the like).

The teleoperational assembly 12 supports and manipulates the medical instrument system 14 while the surgeon S views the surgical site through the console 16. An image of the surgical site can be obtained by an endoscope 15, such as a stereoscopic endoscope, which can be manipulated by the teleoperational assembly 12 to orient the endoscope 15. An electronics cart 18 can be used to process the images of the surgical site for subsequent display to the surgeon S through the surgeon's console 16. The number of medical instrument systems 14 used at one time will generally depend on the diagnostic or surgical procedure and the space constraints within the operating room among other factors. The teleoperational assembly 12 may include a kinematic structure of one or more non-servo controlled links (e.g., one or more links that may be manually positioned and locked in place, generally referred to as a set-up structure) and a teleoperational manipulator. The teleoperational assembly 12 includes a plurality of motors that drive inputs on the medical instrument system 14. These motors move in response to commands from the control system (e.g., control system 20). The motors include drive systems which when coupled to the medical instrument system 14 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like.

The teleoperational medical system 10 also includes a control system 20. The control system 20 includes at least one memory and at least one processor (not shown), and typically a plurality of processors, for effecting control between the medical instrument system 14, the operator input system 16, and an electronics system 18. The control system 20 also includes programmed instructions (e.g., a computer-readable medium storing the instructions) to implement some or all of the methods described in accordance with aspects disclosed herein. While control system 20 is shown as a single block in the simplified schematic of FIG. 1A, the system may include two or more data processing circuits with one portion of the processing optionally being performed on or adjacent the teleoperational assembly 12, another portion of the processing being performed at the operator input system 16, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 20 supports wireless communication protocols such as Bluetooth, IrDA, HomeRF, IEEE 802.11, DECT, and Wireless Telemetry.

In some embodiments, control system 20 may include one or more servo controllers that receive force and/or torque feedback from the medical instrument system 14. Responsive to the feedback, the servo controllers transmit signals to the operator input system 16. The servo controller(s) may also transmit signals instructing teleoperational assembly 12 to move the medical instrument system(s) 14 which extend into an internal surgical site within the patient body via openings in the body. Any suitable conventional or specialized servo controller may be used. A servo controller may be separate from, or integrated with, teleoperational assembly 12. In some embodiments, the servo controller and teleoperational assembly are provided as part of a teleoperational arm cart positioned adjacent to the patient's body.

The teleoperational medical system 10 may further include optional operation and support systems (not shown) such as illumination systems, steering control systems, irrigation systems, and/or suction systems. In alternative embodiments, the teleoperational system may include more than one teleoperational assembly and/or more than one operator input system. The exact number of manipulator assemblies will depend on the surgical procedure and the space constraints within the operating room, among other factors. The operator input systems may be collocated or they may be positioned in separate locations. Multiple operator input systems allow more than one operator to control one or more manipulator assemblies in various combinations.

Figure 1B:
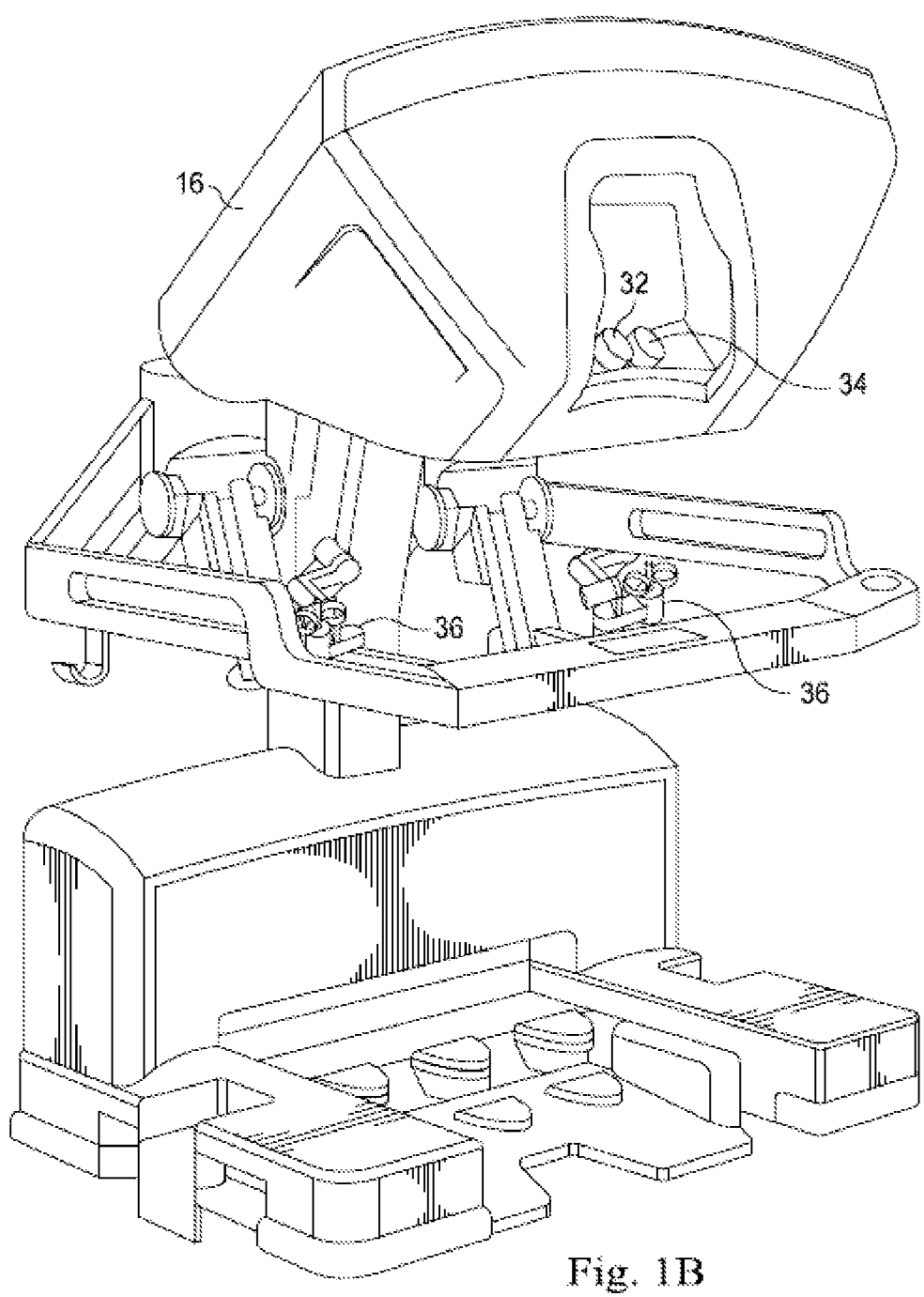
FIG. 1B is a perspective view of a surgeon's control console for a teleoperational medical system, in accordance with many embodiments.

FIG. 1B is a perspective view of the surgeon's console 16. The surgeon's console 16 includes a left eye display 32 and a right eye display 34 for presenting the surgeon S with a coordinated stereo view of the surgical site that enables depth perception. The console 16 further includes one or more input control devices 36, which in turn cause the teleoperational assembly 12 to manipulate one or more tools. The input control devices 36 can provide the same degrees of freedom as their associated instruments 14 to provide the surgeon S with telepresence, or the perception that the input control devices 36 are integral with the instruments 14 so that the surgeon has a strong sense of directly controlling the instruments 14. To this end, position, force, and tactile feedback sensors (not shown) may be employed to transmit position, force, and tactile sensations from the instruments 14 back to the surgeon's hands through the input control devices 36.

Figure 1C:
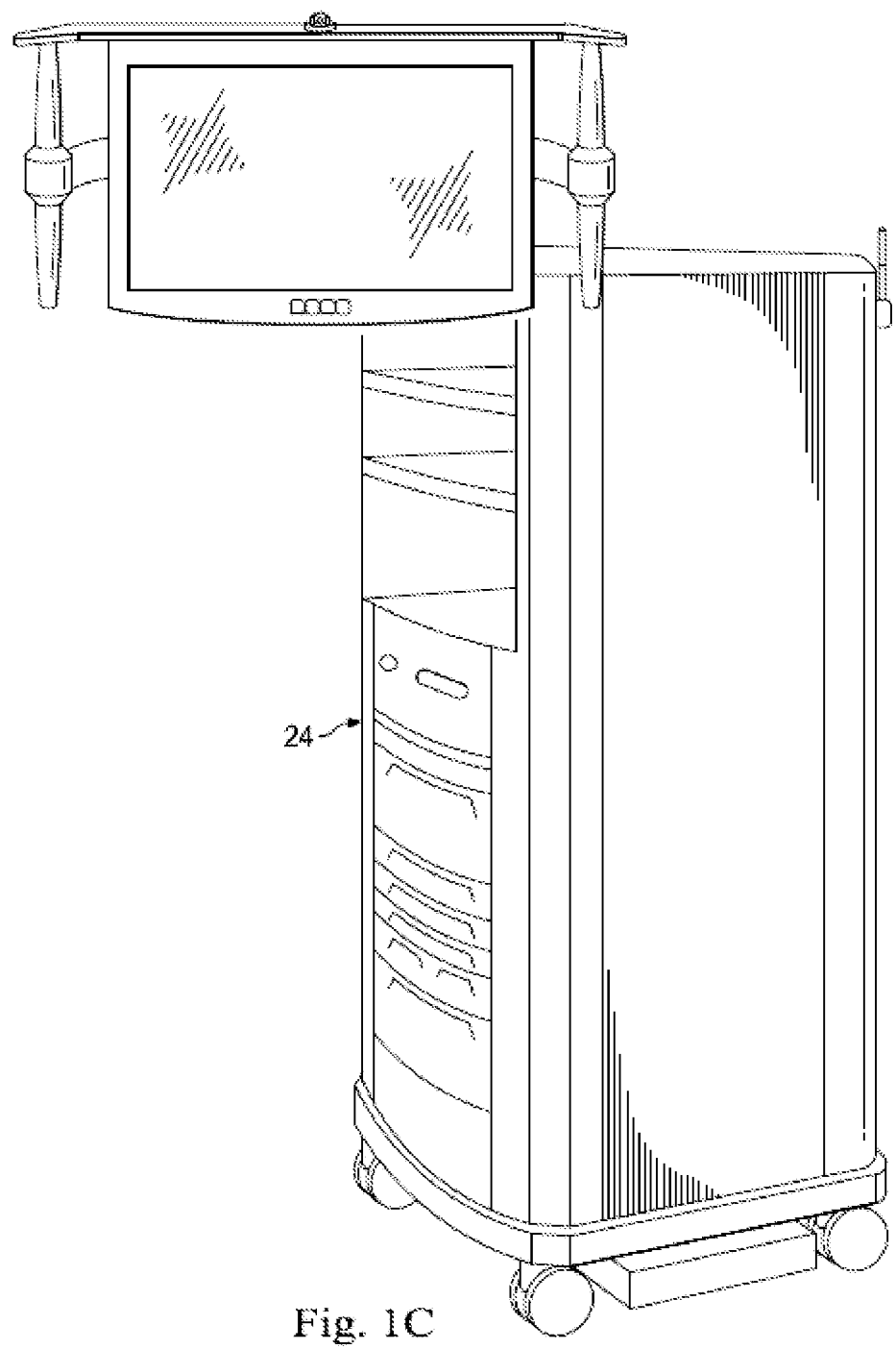
FIG. 1C is a perspective view of a teleoperational medical system electronics cart, in accordance with many embodiments.

FIG. 1C is a perspective view of the electronics cart 18. The electronics cart 18 can be coupled with the endoscope 15 and can include a processor to process captured images for subsequent display, such as to a surgeon on the surgeon's console, or on another suitable display located locally and/or remotely. For example, where a stereoscopic endoscope is used, the electronics cart 15 can process the captured images to present the surgeon with coordinated stereo images of the surgical site. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations. The electronics cart 18 may also include a display monitor and components of the control system 20.

Figure 1D:
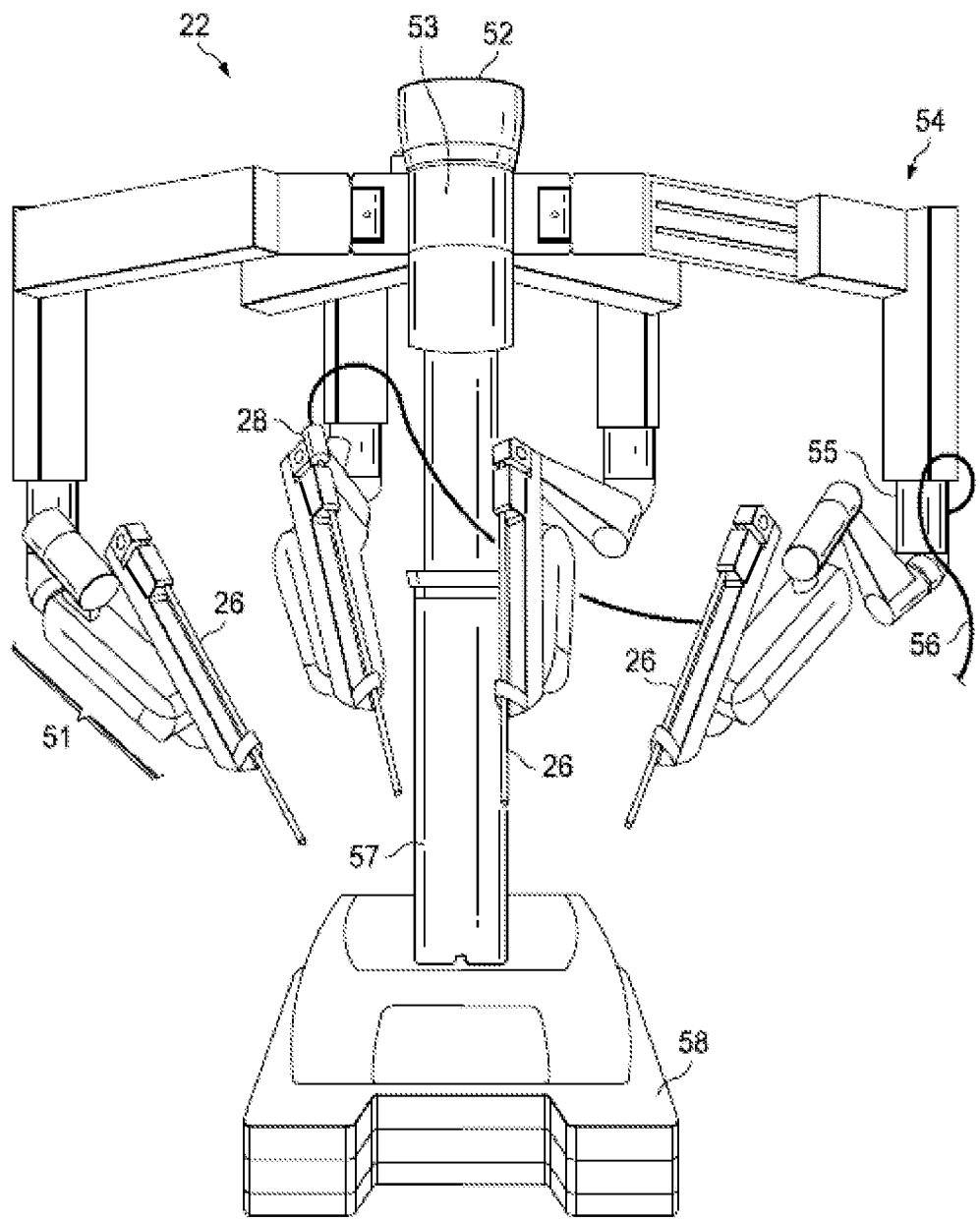
FIG. 1D is a perspective view of a patient side cart, according to one example of principles described herein.

FIG. 1D is a perspective view of a teleoperational assembly 12 which may be referred to as a patient side cart. The patient side cart 12 shown provides for the manipulation of three surgical tools 26 and an imaging device 28, such as a stereoscopic endoscope used for the capture of images of the site of the procedure. The imaging device may transmit signals over a cable 56 to the electronics cart 18. Manipulation is provided by teleoperative mechanisms having a number of joints. The imaging device 28 and the surgical tools 26 can be positioned and manipulated through incisions in the patient so that a kinematic remote center is maintained at the incision to minimize the size of the incision. Images of the surgical site can include images of the distal ends of the surgical tools 26 when they are positioned within the field-of-view of the imaging device 28.

The patient side cart 22 includes a drivable base 58. The drivable base 58 is connected to a telescoping column 57, which allows for adjustment of the height of the arms 54. The arms 54 may include a rotating joint 55 that both rotates and moves up and down. Each of the arms 54 may be connected to an orienting platform 53. The orienting platform 53 may be capable of 360 degrees of rotation. The patient side cart 22 may also include a telescoping horizontal cantilever 52 for moving the orienting platform 53 in a horizontal direction.

In the present example, each of the arms 54 connects to a manipulator arm 51. The manipulator arms 51 may connect directly to a medical instrument 26. The manipulator arms 51 may be teleoperatable. In some examples, the arms 54 connecting to the orienting platform are not teleoperatable. Rather, such arms 54 are positioned as desired before the surgeon 18 begins operation with the teleoperative components.

Figure 2:
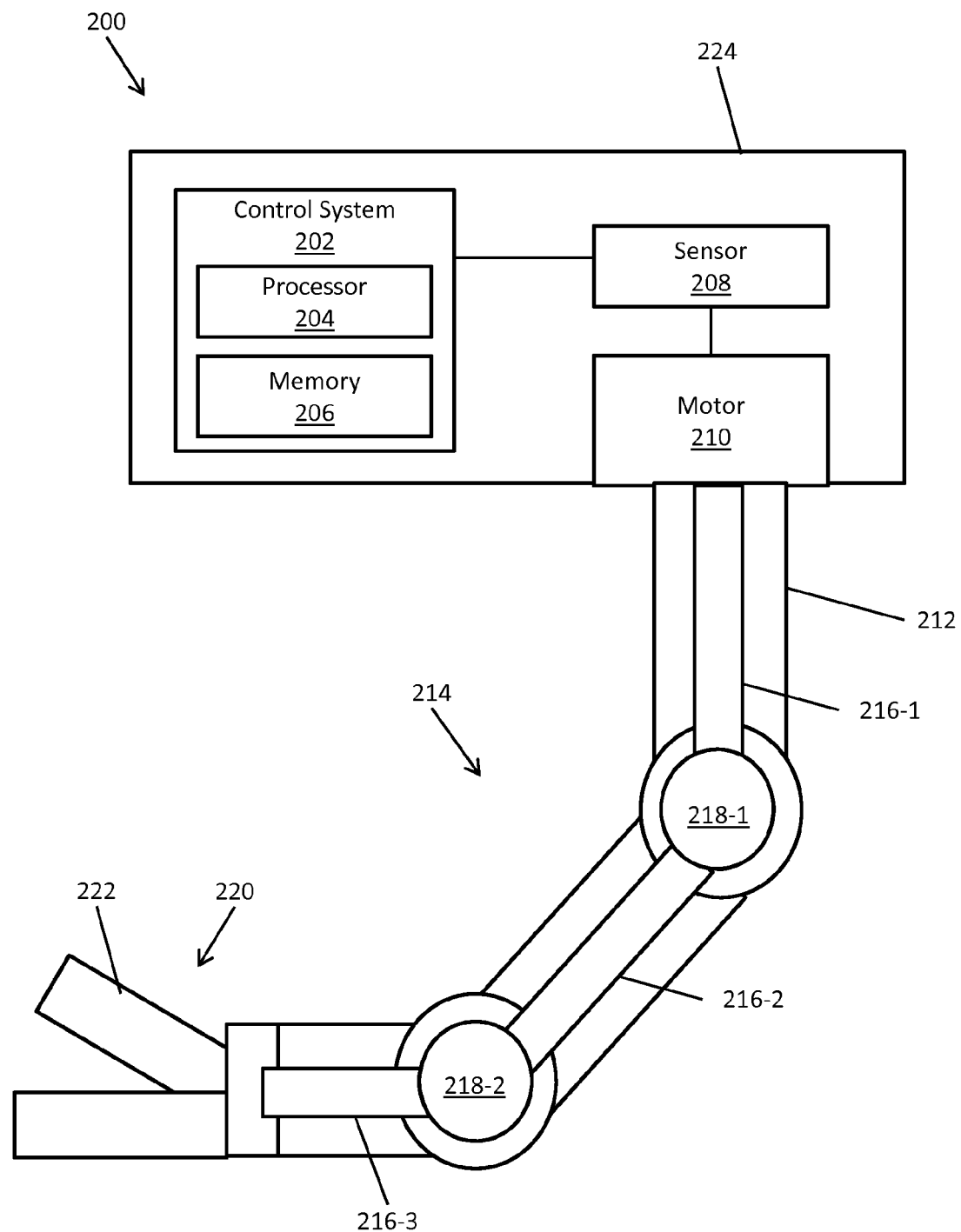
FIG. 2 is a diagram illustrating a medical instrument driven by a motor, according to one example of principles described herein.

FIG. 2 is a diagram illustrating a system 200 that includes a medical instrument 220 driven by a motor 210. According to the present example, the system 200 includes a chassis 224 having a control system 202, a sensor 208, and the motor 210. The system 200 also includes a manipulator arm 212 that includes a drive system 214. The drive system 214 includes drive-shafts 216 and universal joints 218. The drive system 214 connects the motor 210 to the stapler instrument 220.

The stapler instrument 220 can be used to staple tissue together. The stapler instrument 220 includes a clamping mechanism 222 that clamps two portions of tissue together before the stapler staples those portions together. Thus, such a stapler instrument 222 involves two main operations. The first operation is a clamping operation in which the clamping mechanism 222 clamps down on the tissue to be stapled. The second operation is a staple operation in which the stapler is inserted into the clamped tissue. Various embodiments of such a stapler are described in U.S. patent application Ser. No. 14/154,075 (filed Jan. 13, 2014) (disclosing "Torque Compensation"); U.S. patent application Ser. No. 14/154,067 (filed Jan. 13, 2014) (disclosing "Clamping Instrument"); and U.S. patent application Ser. No. 14/154,087 (filed Jan. 13, 2014) (disclosing "Motor Assembly"), which are incorporated by reference herein in their entirety.

In the present example, the motor 210 drives the clamping mechanism 222. More specifically, rotation of the motor 210 causes the clamping mechanism 222 to perform the clamping operation. Rotational force, which is referred to as torque, provided by the motor 210 is transferred through the drive system 214 to the stapler instrument 220. The stapler instrument may include a mechanism, such as a leadscrew, that transfers the rotational force provided by the motor into a linear force applied by the clamping mechanism 222.

The drive system 214 includes a set of drive-shafts 216 and universal joints 218 positioned within the manipulator arm 212. The motor 210 is connected to a first drive-shaft 216-1. Thus, rotation of the motor 210 causes rotation of the first drive-shaft 216-1. The first drive-shaft 216-1 is connected to a second drive-shaft 216-2 through a first universal joint 218-1. The first universal joint 218-1 thus transfers the rotary motion of the first drive-shaft 216-1 to the second drive-shaft 216-2. The second drive-shaft 216-2 is connected to a third drive-shaft 216-3 through a second universal joint 218-2. The second universal joint 218-2 thus transfers the rotary motion of the second drive-shaft 216-2 to the third drive-shaft 216-3. The third drive-shaft 216-3 is connected to the clamping mechanism 222 of the stapler instrument 220.

When using a universal joint, the angle between two adjoining drive-shafts causes the output drive-shaft to rotate at a varying velocity despite a constant rotational velocity of the input shaft. For example, a constant rotation of the first drive-shaft 216-1 causes a varying rotation of the second drive-shaft 216-2. Similarly, rotation of the third drive-shaft 216-3 is further varied due to the angle between the second drive-shaft 216-2 and third drive-shaft 216-3. Thus, the drive system 214, when connected to the motor 210, places a load on the motor 210 that causes torque ripples. The torque ripple creates an oscillation component in the torque output.

The control system 202 is used to control the motor 210 and to ensure that the torque output of the motor 210 does not exceed a predefined limit. For example, if the torque output exceeds such a limit, it may indicate that the clamping operation was not performed correctly. The control system 202 receives data from a sensor 208 that measures the torque output of the motor 210. The control system 202 then compares the measured torque output with the torque limit. According to principles described herein, the control system 202 determines a torque ripple, or oscillation component, of the torque output. In real time, the control system 202 adjusts the torque limit to create a dynamic torque limit. The control system 202 can then compare the torque output to the dynamic torque limit. Doing so provides a more accurate determination as to whether the torque output is acceptable and allows the controller to compensate for oscillations while controlling the base component of the torque limit.

The control system 202 includes a processor 204 and a memory 206. The memory may include various types of memory including volatile memory (such as Random Access Memory (RAM)) and non-volatile memory (such as solid state storage). The memory 206 may store computer readable instructions, that when executed by the processor 204, cause the control system 202 to perform various functions, including the functions described herein. The memory 206 may also store data representing the torque output, a torque limit, a dynamic torque limit, and other data points.

While FIG. 2 illustrates the control system 202, the sensor 208, and the motor 210 all within the same chassis 224, other embodiments may be configured differently. For example, in some embodiments, the control system 202 may be located elsewhere yet still be in communication with the sensor 208. Moreover, while FIG. 2 illustrates a double universal joint drive system 214, other embodiments may have a single universal joint drive system or a drive system with more than two universal joints.

Figure 3A:
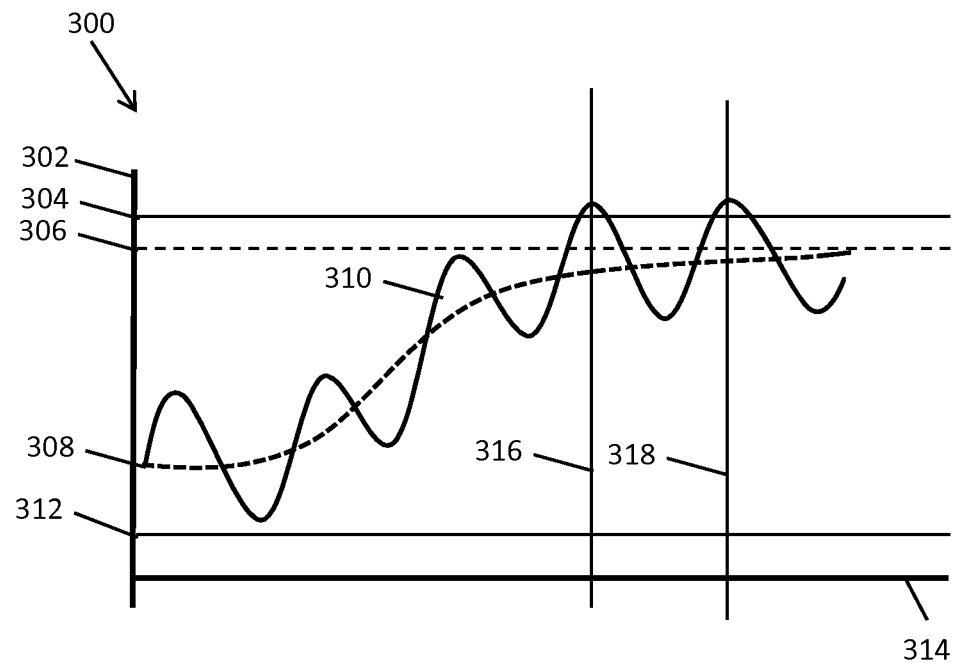
FIG. 3A is a graph showing a torque output with respect to a torque limit, according to one example of principles described herein.

FIG. 3A is a graph 300 showing torque output 310 of a motor (e.g., motor 210, FIG. 2). According to the present example, the vertical axis 302 represents motor torque and the horizontal axis 314 represents time. The graph 300 shows a target torque 306, an upper torque limit 304, and a lower torque limit 312.

The target torque 306 represents a torque level that is desired to perform a particular operation. For example, in order to perform the clamping operation correctly, it may be known that the torque output 310 of the motor should reach a certain torque level. This torque level is defined as the target torque 306. In some examples, the target torque 306 may be defined as a range of torque levels.

The upper torque limit 304 represents a torque level that if reached, may indicate that an operation did not perform correctly. In other words, if the torque output 310 exceeds such a level, it may be an indication that tissue was not clamped as desired within the clamping mechanism. This may be important for an operator of the stapler to know because the staple operation should not be performed if the tissue is not appropriately clamped within the clamping mechanism. The lower torque limit 312 may perform a similar function.

The motor torque output 310 includes a base component 308 and an oscillation component which is the difference between the torque output 310 and the base component 308. The base component 308 is analogous to a Direct Current (DC) component of an electrical signal. The oscillation component is analogous to an Alternating Current (AC) component of an electrical signal. The oscillation component is caused by the torque ripple experienced by the motor. As described above, the load placed on the motor by the drive system can cause the torque ripple. Additionally, as the drive system changes position, the torque ripple will be affected. Specifically, as the manipulator arm moves, the angle at which the drive-shafts meet will change. Because the torque ripple is affected by the angle at which the drive-shafts meet, the torque ripple will change as the angle changes.

The torque ripple experienced by the motor may itself have several components. Torque ripples may be further decomposed into torque harmonics. For example, some torque outputs may represent a combination of a 1× torque harmonic, a 2× torque harmonic, and a 4× torque harmonic. Torque harmonics represent deviations in the torque output at the spatial frequencies that are integer multiples of the inverse of one mechanical revolution of the motor. For example, a 1× torque harmonic may look like a single sine wave across one period of rotor rotation. A 2× torque harmonic may look like two full sine waves across one period of rotor rotation.

It is desirable that the base component 308 approach the target torque without exceeding the upper torque limit 304. But, with the oscillation component caused by the torque ripple, there may be time points 316, 318 at which the torque output 310 exceeds the torque limit 304. According to principles described herein, this issue is mitigated by locally changing the torque limit 304 to account for the oscillation component. Localized modified torque limit for a limited duration, rather than uniform upward of the entire torque limit, allows the target torque to remain at a level needed to provide the maximum operating forces for the driven instrument, for example, the forces needed to clamp the maximum amount of tissue.

Figure 3B:
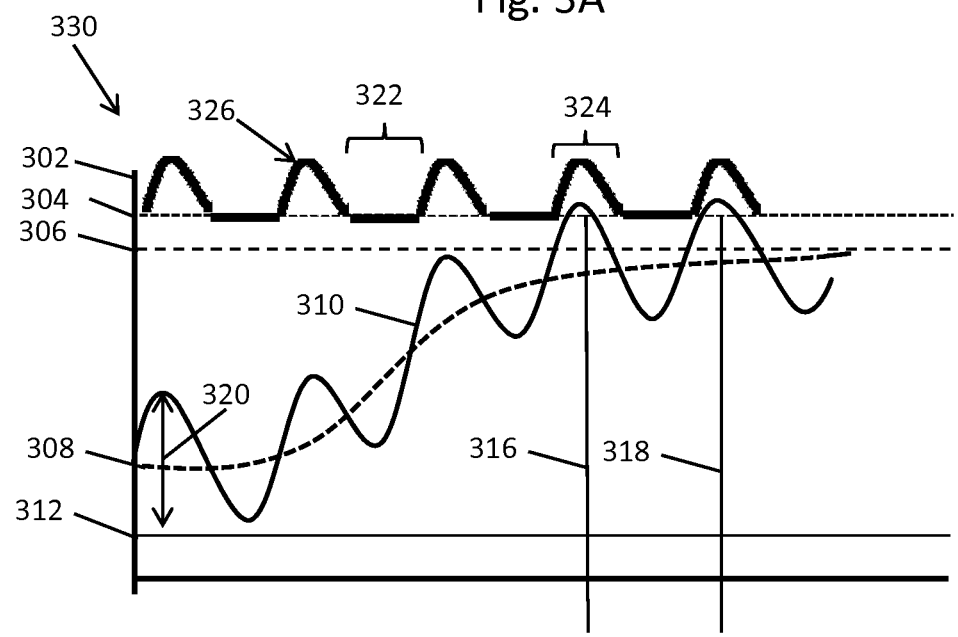
FIG. 3B is a diagram showing an illustrative compensated torque limit, according to one example of principles described herein.

FIG. 3B is a graph 330 showing a dynamic torque limit 326. According to the present example, the torque limit 304 is adjusted to create the dynamic torque limit 326. This may be done by determining characteristics of the oscillation component such as period, phase, and amplitude 320. The torque limit 304 can then be locally adjusted based on these characteristics to create the dynamic torque limit 326. For example, the varying amplitude of the oscillation may be added to the torque limit over a portion of the period of the oscillation (e.g., a portion where the oscillation amplitude is greater than the base component). Alternatively, a predetermined percentage of the amplitude may be added to the torque limit over a portion of the period of the oscillation. Alternatively, the peak amplitude of the oscillation may be added to the torque limit over a portion of the period of the oscillation. In the embodiment of FIG. 3B, the dynamic torque limit has a clipped sinusoidal profile, but other profiles that provide local variation of the torque limit based on the period, phase, and/or amplitude of the oscillation component may be used as the dynamic torque limit.

In the example of FIG. 3B, the dynamic upper torque limit 326 appears as a clipped sinusoidal wave. Specifically, the dynamic torque limit has two types of components. During a first duration component 322 the torque limit matches the original torque limit 304. During the second duration component 324, however, the torque limit is increased based on the detected oscillation component of the torque output 310. Thus, at time points 316 and 318, the torque output 310 does not exceed the dynamic torque limit 326, even though it does exceed the original torque limit 304. Thus, the system does not erroneously indicate that the relevant portion (i.e., base component 408) of the torque output has exceeded the torque limit 304 while the system is capable of handling oscillations. In various embodiments, a dynamic lower torque limit may be determined by adjusting the lower torque limit 312 based on the oscillation component.

Figure 4:
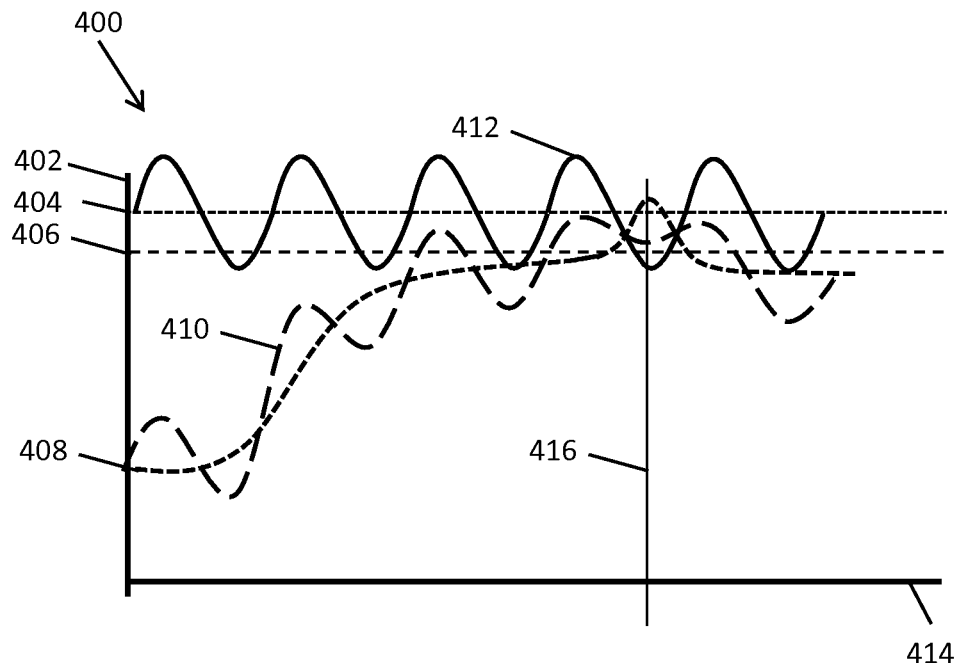
FIG. 4 is a graph showing an illustrative compensated torque limit, according to one example of principles described herein.

FIG. 4 is a graph 400 showing an illustrative full sinusoidal dynamic torque limit 412. Again, the vertical axis 402 represents motor torque and the horizontal axis 414 represents time. The torque output 410 of the motor includes a base component 408 and an oscillation component. The graph 400 illustrates a target torque 406 and a torque limit 404.

In this example, the dynamic torque limit 412 can be created by adding the oscillation component of the torque output 410 to the original torque limit 404. Thus, the dynamic torque limit 412 appears as a sinusoidal wave that matches the oscillation component of the torque output 410. Providing a dynamic torque limit across the full period of the oscillation may be useful in certain applications. For example, a spike may occur in the base component 408 of the motor torque 410 at a time point 416 that coincides with a lower portion of the oscillation component. This may cause the torque output 410 not to exceed the torque limit 404 even though the base component 408 exceeds the torque limit 404. In such a case, the system should alert the operator that the clamping operation may have failed but the system does not do so. The torque output 410 does exceed the dynamic torque limit 412. Basing an alert on the dynamic torque limit 412, however, would appropriately indicate that the relevant portion (i.e., base component) of the torque output exceeds the torque limit 404.

Compensating for the oscillation component of the torque output 410 may be performed by the control system (e.g. 202, FIG. 2) in a variety of ways. The control system stores a digital representation of the torque output 410 and a digital representation of the torque limit 404. If, at a particular point in time, the value of the torque output 410 exceeds the value of the torque limit 404, then the system can alert the operator accordingly. But by adjusting the torque limit 404 as described above, the control system is essentially adjusting the mathematical difference between the value of the torque output 410 and the value of the torque limit 404. Specifically, by adding the value or a partial value of the oscillation component to the value of the torque limit, the dynamic torque limit 412 is created. In some examples, however, instead of adding the value of the oscillation component to the torque limit 404, the control system can perform the same function by subtracting the oscillation component from the digital representation of the torque output 410. Thus, while the actual torque output 410 still exhibits the oscillation component, the digital representation of the torque output 410 does not. Subtracting the oscillation component form the digital representation of the torque output 410 thus adjusts the mathematical difference between the torque output 410 and the torque limit 404 in the same manner as adding the oscillation component to the torque limit 404 to create the dynamic torque limit 412.

Figure 5:
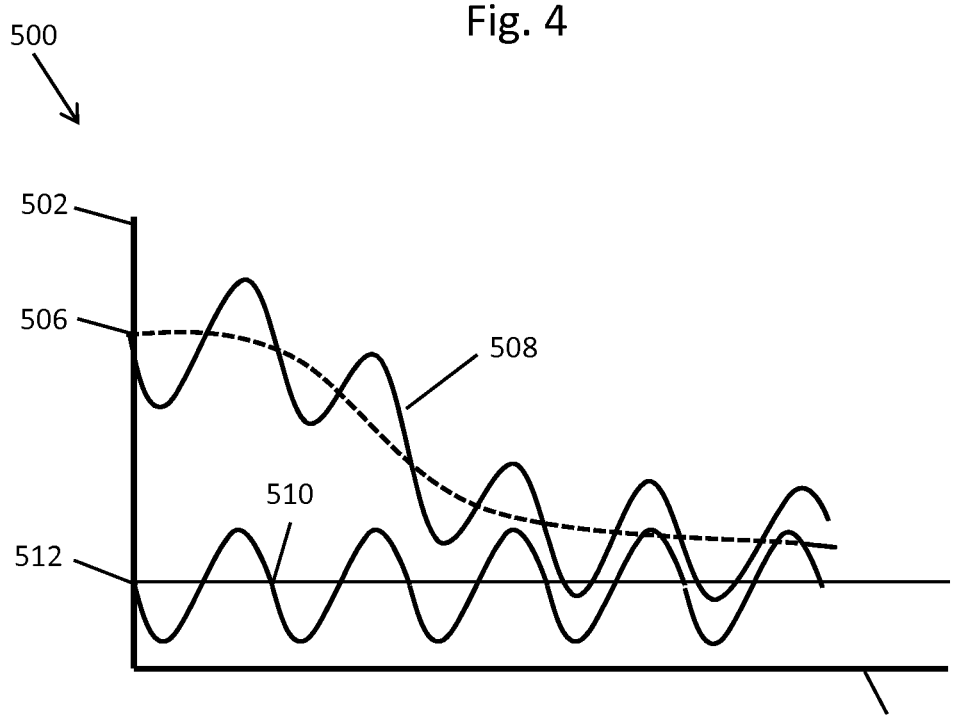
FIG. 5 is a graph showing an illustrative compensated torque limit for a lower torque limit, according to one example of principles described herein.

FIG. 5 is a graph 500 showing an illustrative dynamic torque limit 510 for a lower torque limit 512. Again, the vertical axis 502 represents motor torque and the horizontal axis 504 represents time. The torque output 508 of the motor includes a base component 506 and an oscillation component. In some cases, it may be desirable to ensure that the torque output does not drop below a certain level. Thus, a lower torque limit 512 can be used instead of an upper torque limit as illustrated in FIGS. 3A, 3B, and 4. As with the upper torque limit, the control system determines the oscillation component of the torque output 508 and uses information related to the oscillation component to create an adjusted lower torque limit 510. Thus, while the torque output 508 may drop below the lower torque limit 512 due to the torque ripple, the torque output does not drop below the dynamic lower torque limit 510.

Figure 6:
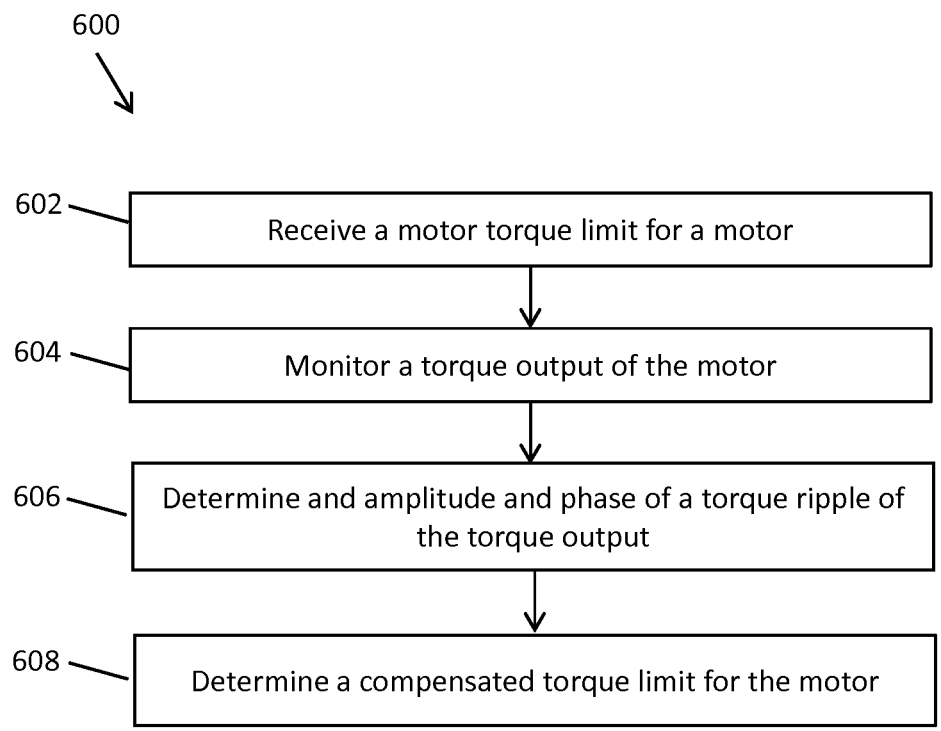
FIG. 6 is a flowchart showing an illustrative method for adjusting a torque limit based on a torque ripple, according to one example of principles described herein.

FIG. 6 is a flowchart showing an illustrative method 600 for adjusting a torque limit based on a torque ripple. According to the present example, the method 600 includes a step 602 for receiving a motor torque limit for a motor. As described above, the control system may receive the torque limit for a particular type of operation such as the clamping operation of a stapler instrument. The torque limit is based on a known torque level that if reached, may indicate that the clamping operation was not performed successfully.

The method 600 further includes a step 604 for monitoring the torque output of the motor. This may be done through use of a sensor connected to the motor. As described above, the torque output includes a base component and an oscillation component associated with a torque ripple. The torque ripple may be caused in part by the load attached to the motor. Specifically, there may be a system of one or more universal joints connecting the motor to the clamping mechanism. The torque tipple will be affected by changes in positions of those universal joints. Thus, the torque output is monitored in real time.

The method 600 further includes a step 606 for determining an amplitude and phase of the torque ripple of the torque output. In other words, the characteristics of the oscillation component of the torque output are determined. These characteristics will vary in real time as the manipulator arm, which carries the drive-shafts and universal joints, shifts position. Thus, determining the amplitude and phase of the oscillation component is done in real time.

The method 600 further includes a step 608 for determining a dynamic torque limit for the motor. This may be done in a variety of ways as discussed above. Specifically, the amplitude and phase of the torque ripple are used to adjust the received torque limit to create the dynamic torque limit. In one example, the dynamic torque limit appears as a clipped sine wave. In some examples, the dynamic torque limit appears as a full sine wave.

Through use of principles described herein, a more accurate determination of whether the torque output has exceeded a defined limit is achieved. This can be even more useful in situations when a target torque is relatively close to a torque limit and the torque ripple experienced by the motor has a greater effect on the torque output. This can reduce situations in which the control system either wrongfully indicates that the torque limit has been exceeded or improperly abstains from indicating that the torque limit has been exceeded.

One or more elements in embodiments of the invention may be implemented in software to execute on a processor of a computer system such as control processing system. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A medical instrument system comprising:
   a motor; and
   a control system comprising a processor and a memory, the memory comprising machine readable instructions that when executed by the processor, cause the control system to:
   monitor a torque output of the motor;
   determine an oscillation component of the torque output, the oscillation component being associated with a torque ripple;
   receive an upper torque limit;
   adjust the upper torque limit based on the oscillation component to create a localized compensated upper torque limit; and
   output to a user interface, an indication of operation failure in response to a determination that the torque output exceeds the localized compensated upper torque limit.

2. The system of claim 1, further comprising:
   a clamping mechanism; and
   a driveshaft that connects the motor to the clamping mechanism.

3. The system of claim 2, further comprising a stapling mechanism integrated with the clamping mechanism, the stapling mechanism configured to staple tissue clamped by the clamping mechanism.

4. The system of claim 2, wherein the upper torque limit indicates a likely failure of the clamping mechanism.

5. The system of claim 2, wherein the driveshaft is connected to the clamping mechanism through use of at least one universal joint.

6. The system of claim 5, wherein the oscillation component is a function of a position of the universal joint.

7. The system of claim 5, wherein to account for the oscillation component, the control system is configured to adjust the upper torque limit in accordance with the oscillation component.

8. A medical instrument system comprising:
a motor; and
a control system comprising a processor and a memory, the memory comprising machine readable instructions that when executed by the processor, cause the control system to:
receive a motor torque limit for the motor;
monitor a torque output of the motor;
determine an amplitude and a phase of a torque ripple of the torque output; and
determine a locally compensated torque limit for the motor by adjusting the motor torque limit based on the determined amplitude and phase of the torque ripple.

9. The system of claim 8, wherein the locally compensated torque limit includes a first component at the motor torque limit and a second component at an adjusted torque limit.

10. The system of claim 8, wherein the locally compensated torque limit includes an alternating pattern of first and second components.

11. The system of claim 8, wherein to monitor the torque output, the control system is further made to receive information from a sensor regarding a position of the motor.

12. The system of claim 8, wherein the control system is further made to output to a user interface an indication of operation failure in response to determining that the torque output exceeds the locally compensated torque limit.

13. The system of claim 8, wherein the motor drives a stapler clamping mechanism.

14. The system of claim 8, wherein the motor is coupled to a drive system that includes a universal joint.

15. The system of claim 8, wherein the motor torque limit is an upper motor torque limit.

* * * * *